United States Patent [19]

Pregozen

[11] Patent Number: 5,141,803
[45] Date of Patent: Aug. 25, 1992

[54] NONWOVEN WIPE IMPREGNATING COMPOSITION

[75] Inventor: David Pregozen, Park Ridge, N.J.

[73] Assignee: Sterling Drug, Inc., New York, N.Y.

[21] Appl. No.: 750,716

[22] Filed: Aug. 20, 1991

Related U.S. Application Data

[63] Continuation of Ser. No. 212,848, Jun. 29, 1988, abandoned.

[51] Int. Cl.$^5$ .......................... A61K 9/70; C11D 3/48
[52] U.S. Cl. ................................. 428/288; 15/104.93; 15/209.1; 206/812; 252/106; 424/404; 428/289; 514/635
[58] Field of Search ............... 15/104.93, 209 R; 206/812; 252/106; 424/404; 428/288, 289

[56] References Cited

U.S. PATENT DOCUMENTS

| | | | |
|---|---|---|---|
| 3,264,188 | 8/1966 | Gresham | 167/84 |
| 4,017,002 | 4/1977 | Doyle et al. | |
| 4,587,266 | 5/1986 | Verdicchio | 514/635 |
| 4,615,937 | 10/1986 | Bouchette | 428/288 |
| 4,678,704 | 7/1987 | Fellows | 428/289 |
| 4,732,797 | 3/1988 | Johnson et al. | 428/74 |
| 4,775,582 | 10/1988 | Abba et al. | 428/290 |
| 4,781,974 | 11/1988 | Bouchette et al. | 428/288 |
| 4,837,079 | 6/1989 | Quantrille et al. | 428/288 |

Primary Examiner—James C. Cannon
Attorney, Agent, or Firm—John R. Everett

[57] ABSTRACT

An aqueous composition for impregnating a nonwoven wipe having a pH of from 3.5 to 4.5 and containing a preservative system comprising potassium sorbate, citric acid, disodium EDTA and a cationic biocide selected from polyhexamethylene biguanide hydrochloride and poly[oxyethylene(dimethyliminio)ethylene(dimethyliminio)ethylene dichloride]; and a moistened wipe, impregnated with the aqueous composition, useful for cleaning or delivering active ingredients to animate and inanimate surfaces.

14 Claims, No Drawings

NONWOVEN WIPE IMPREGNATING COMPOSITION

This is a continuation of application Ser. No. 212,848, filed Jun. 29, 1988, now abandoned.

BACKGROUND OF THE INVENTION

1. Field of the Invention

The invention relates to nonwoven wet wipes and more specifically to nonwoven wipes impregnated with an aqueous non-alcoholic composition in which the preservative system for the impregnated wipe comprises potassium sorbate, citric acid, disodium ethylenediaminetetraacetate and a cationic agent selected from polyhexamethylene biguanide hydrochloride and poly-[oxyethylene(dimethylimino)ethylene(dimethyliminio)ethylene dichloride].

2. Information Disclosure Statement

Various forms of nonwoven impregnated wipes are available and have been suggested for performing a wide variety of tasks, such as for cleaning hard surfaces, cleansing the hands and other areas of the body and delivering active ingredients to various surfaces, both animate and inanimate.

In the case of nonwoven impregnated wipes adapted for cleaning hard and skin surfaces, the impregnant generally is aqueous based. Such wipes are marketed ready for use either in individual packet form or in bulk form in suitable dispensers from which individual wipes can be withdrawn as needed. Whatever the form of packaging, the wipes are stored for substantial periods of time prior to use and therefore need to be protected against microbial contamination and deterioration to which they are readily susceptible. One common method to achieve this is to incorporate a suitable chemical preservative system in the liquid composition employed to impregnate the nonwoven wipe.

Preservative systems which have been employed in a number of aqueous impregnating compositions for nonwoven wipes have included ethyl alcohol which is well known for its antiseptic effect. One such preservative system which has provided excellent results comprises sorbic acid, citric acid and ethyl alcohol. However, the ethyl alcohol generally is employed in such preservative systems at concentrations above five weight-percent of the impregnating composition.

Presently there is a trend to formulate impregnating compositions for nonwoven wipes which avoids the use of ethyl alcohol because manufacturers of wet/moist wipes perceive that many consumers would prefer alcohol-free wipes, particularly those which are primarily intended for use in personal hygiene, especially baby wash cloths for which there is a substantial market. However, a problem arises in eliminating ethyl alcohol from sorbic acid - citric acid - ethyl alcohol preservative systems for nonwoven wipes in that the combination containing only sorbic acid and citric acid does not always provide adequate protection against microbial contamination and deterioration.

U.S. Pat. No. 4,732,797 discloses a liquid preserving composition for a fibrous wiper consisting essentially of a mixture of citric acid and sorbic acid as the preservative component, water and optionally ingredients selected from skin moisturizers and fragrances.

Wipers having incorporated therein a cationic antimicrobial agent have been described, for example, in U.S. Pat. Nos. 3,264,188, 4,615,937 and 4,678,704, discussed hereinbelow.

U.S. Pat. No. 3,264,188 discloses a sanitary impregnated skin wiper for proctological use comprising a facial grade creped tissue having dispersed therethrough a mineral oil and an emulsifier such as triethanolamine oleate, which wiper may include a bacteriostatic agent, benzalkonium chloride being a preferred bacteriostatic agent.

U.S. Pat. No. 4,615,937 discloses an antimicrobially active nonwoven web wherein the antimicrobial agent is substantive both to the fibers and the binder in the web and preferably is an organo-silicon quaternary ammonium salt.

U.S. Pat. No. 4,678,704 discloses an impregnated fabric material comprising a fabric substrate, which may be woven or nonwoven, to which has been bonded an active cationic impregnant and an anionic indicator dye in combination with a further cationic component. Nonionic surfactants, chelating agents and fragrances may also be included in the impregnated fabric. Examples of the cationic materials which are disclosed are quaternary ammonium compounds, bisguanides and polymeric bisguanide such as polyhexamethylene bisguanide hydrochloride.

U.S. Pat. No. 4,587,266 discloses the use of polyhexamethylene biguanide hydrochlorides as antimicrobial agents in combination with certain amine oxides in aqueous antimicrobial compositions. The polyhexamethylene biguanide hydrochlorides are identified as being commercially available from ICI Americas Inc. under the tradename Cosmocil CQ.

A currently commercially available personal cleansing wipe product lists its key ingredients and their functions as follows:

| KEY INGREDIENT | FUNCTION |
| --- | --- |
| Demineralized Water | Moisturizes tender skin |
| Propylene Glycol | |
| PEG-75 Lanolin* | Softens skin |
| Cocoamphodiacetate | Cleans and soothes skin |
| Polysorbate 20 | |
| Methylparaben | Maintains product purity |
| 2-Bromo-2-nitropropane-1,3-diol | and freshness |
| Propylparaben | |
| Fragrance | Pleasant non-irritating scent |

*a polyethylene glycol derivative of lanolin with an average of 75 moles of ethylene oxide

SUMMARY OF THE INVENTION

In order to enhance the antimicrobial effect of the combination of sorbic acid and citric acid in a preservative system for moist nonwoven wipes, various types of commercially available cationic biocides were investigated for inclusion in the preservative system because of their well known substantivity for nonwoven fabrics. Unfortunately, the inclusion of the cationic biocides resulted in an undesirable slippery feel being imparted to the impregnated nonwoven wipe, especially those wipes the fiber content of which contains a significant portion of rayon or rayon-polyester blends. However, it was surprisingly found that incorporation of either of two specific cationic biocides greatly minimized the slippery feel of the wet wipe.

Thus in one aspect of the invention there is provided an aqueous composition for impregnating a nonwoven wipe comprising from about 0.02 to about 0.25 weight-percent of potassium sorbate, from about 0.05 to about 0.20 weight-percent of citric acid, from about 0.02 to about 0.20 weight-percent of disodium ethylenediaminetetraacetate, from about 0.03 to about 0.24 weight-percent of a cationic biocide selected from the group consisting of (a) polyhexamethylene biguanide hydrochloride and (b) poly[oxyethylene(dimethyliminio)ethylene(dimethyliminio)ethylene dichloride]; and the remainder to 100 weight-percent water, wherein the pH of the composition is from about 3.5 to about 4.5.

In another aspect of the invention there is provided a moistened wipe comprising a flexible absorbent nonwoven substrate impregnated with the aqueous composition defined hereinabove.

DETAILED DESCRIPTION OF THE INVENTION INCLUDING THE PREFERRED EMBODIMENTS

The aqueous composition of the invention is employed as an impregnant for flexible absorbent nonwoven fabrics in the manufacture of moist wipes useful for cleaning and/or delivering active agents to animate or inanimate surfaces. The aqueous composition is comprised of water having dissolved therein a preservative system specifically adapted to prevent microbial deterioration of the moist wipe, which is readily susceptible to microbial deterioration in the absence of a suitable preservative. The preservative system is comprised of potassium sorbate, disodium ethylenediaminetetraacetate (disodium EDTA), a cationic biocide selected from two specific agents described more fully hereinbelow and citric acid.

The potassium sorbate is employed in the aqueous composition at a concentration of from about 0.02 to about 0.25 percent by weight of the aqueous composition. The antimicrobial effect contributed by the sorbate is due primarily to sorbic acid to which the sorbate is converted in situ at the pH level employed in the aqueous composition as discussed hereinbelow.

The disodium ethylenediaminetetraacetate enhances the effect of the preservative system. It is employed at a concentration of from about 0.02 to about 0.20 percent by weight of the composition.

The cationic biocide is selected from polyhexamethylene biguanide hydrochloride and poly[oxyethylene(dimethyliminio)ethylene(dimethyliminio)ethylene dichloride]. Polyhexamethylene biguanide hydrochloride is a known biocide with a wide spectrum of antimicrobial activity and is commercially available as a 20% w/w aqueous solution from ICI Americas Inc., Wilmington Del. under the tradename COSMOCIL CQ. It can be represented by the general formula:

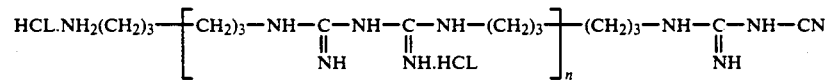

in which n has an average value such that the molecular weight is 1000–1400. Poly[oxyethylene(dimethyliminio)ethylene(dimethyliminio)ethylene dichloride] is a known broad spectrum microbiocide and is commercially available as a 60% aqueous concentrate from Buckman Laboratories, Inc., Memphis, Tenn. under the tradename WSCP. It has a repeat unit structure as follows:

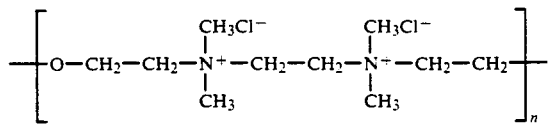

in which n has an average value such that the molecular weight is 3000–4000. The cationic biocides are employed at a concentration of from about 0.03 to about 0.24 percent by weight (active basis) of the aqueous composition.

The pH of the aqueous composition should be in the range of from about 3.5 to about 4.5 and preferably from about 4.0 to about 4.3. As disclosed hereinbefore, the antimicrobial activity derived from the use of potassium sorbate is due primarily to undissociated sorbic acid which is formed in situ in the pH range of 3.5 to 4.5. Citric acid is employed in the aqueous composition as a pH adjuster in an amount that ensures that the pH of the aqueous composition will fall in the range of from about 3.5 to about 4.5. A pH in this range can be obtained when citric acid is employed at a concentration of from about 0.05 to about 0.20 percent by weight of the aqueous composition.

Depending on the particular use intended for a wipe impregnated with the aqueous composition of the invention, optional ingredients may be included in the aqueous composition.

Thus a wipe intended for cleansing the skin may include skin moisturizers/humectants such as propylene glycol, glycerin and sorbitol; skin softeners/emollients such as ethoxylated lanolin, ethoxylated glucose, silicone oils, mineral oil and fatty acid esters; botanical extracts such as witch hazel extract, aloe vera gel and chamomile extract; and perfumes and fragrances. The concentrations of such optional ingredients will, based on the weight of the final composition, fall in the ranges of 0.2 to 10 weight-percent for skin moisturizers and humectants, 0.02 to 5 weight-percent for skin softeners and emollients, 0.01 to 50 weight-percent for botanical extracts and 0.01 to 2 weight-percent for perfumes and fragrances.

Surfactants and cleansers optionally may also be included in the aqueous compositions of the invention. The surfactant may be an amphoteric, such as cocoamphodiacetate which is commercially available from several sources or a nonionic, such as a polyethylene glycol ether of glycerol cocoate, polyoxyethylene polyoxypropylene block polymers, or a polymer of dimethylsiloxane with polyoxyethylene and/or polyoxypropylene side chains, all commercially available. The surfactant will generally be employed at a concentration of 0.02 to 10 percent by weight based on the weight of the aqueous composition.

The substrate employed in the moistened wipe of the invention is a fibrous flexible absorbent nonwoven sheet material consisting essentially of cellulosic fibers or blends of cellulosic fibers such as rayon and cotton fibers or blends of such cellulosic fibers with one or more synthetic fibers such as polypropylene, polyethylene, polyester and nylon fibers. Such blends may also include wood pulp fibers. Binders generally are employed to bind together the fibers thus ensuring that the finished nonwoven sheet has adequate wet strength. Such binders are, for example, acrylic polymers, ethylene vinyl acetate polymers, vinyl acetate copolymers and styrene butadiene polymers. Such nonwoven materials and processes for their manufacture are well known in the art. Processes for manufacturing such nonwoven sheet materials include carding, air laying, water entanglement, thermal bonding and wet laying.

The moistened wipe of the invention can be prepared by applying the aqueous composition according to the invention to the flexible absorbent nonwoven substrate by a variety of well known methods such as by spraying, padding, printing and gravity application. Preferably the loading of the aqueous composition is from about two times (200%) to about 5 times (500%) the weight of the nonwoven substrate, and more preferably about three and one-half times (350%) the weight of the nonwoven substrate.

The aqueous composition of the invention can be prepared conveniently by the following procedure:

All optional ingredients, except the plant extracts, to be included in the composition are combined and mixed until a clear mixture is obtained. The resulting mix is added with efficient stirring to approximately 95% of the formula amount of water and to this is added with stirring, individually and in the order listed, the plant extract, if any, the disodium ethylenediaminetetraacetate, the cationic biocide and the potassium sorbate. Citric acid is then added to the stirred batch in an amount sufficient to adjust the pH to 3.5 to 4.5. The remainder of the formula amount of water is then added with stirring.

Although the major amount of water employed in the composition is deionized water, it will be appreciated that minor amounts of water are or may be derived from certain commercially available ingredients which are in some cases supplied as aqueous solutions or concentrates.

The moistened wipe of the invention may be used to clean, or deliver active ingredients such as sunscreens, insect repellants, etc., to animate and/or inanimate surfaces. Thus they may be used to clean the hands or other skin areas of the body or as baby wipes during diaper change as well as for cleaning various hard surfaces such as kitchen counter tops, toilet bowls, sinks, etc.

The moistened wipes of the invention should be packaged in a manner which will maintain them in a moist condition. A variety of well known packaging methods are available. For example, they may be individually packaged in moisture impervious envelopes or packaged in bulk form in canisters provided with suitable dispensing openings. When packaged in bulk form they may be provided as separate sheets, e.g., in interleaved form, or in the form of interconnected sheets from which individual sheets readily may be separated. In the latter case, reference is made to U.S. Pat. No. 4,017,002.

The invention is further illustrated by the following examples without, however, being limited thereto.

EXAMPLE 1

An aqueous composition according to the invention was fomulated, using the general procedure described hereinabove, as follows:

| Ingredient | % by Weight |
| --- | --- |
| Propylene Glycol | 0.500 |
| PEG-60 Lanolin (50% solution)[a] | 0.100 |
| Miranol ® C2M Conc. NP-PG (38% active)[b] | 0.100 |
| Perfume | 0.475 |
| Aloe Vera Gel (1:10)[c] | 0.010 |
| Cosmocil CQ (20% active)[d] | 0.700 |
| Potassium Sorbate | 0.140 |
| Disodium EDTA Dihydrate | 0.100 |
| Citric Acid | 0.100 |
| Deionized Water | 97.775 |
| pH 4.1 | 100.000 |

[a]CTFA Adopted Name: commercially available from Croda, Inc., New York, New York under the tradename SOLAN-50% (50% active)
[b]38% aqueous solution (containing a small amount of propylene glycol) commercially available from Miranol Inc., Dayton, New Jersey; active is cocoamphodiacetate that conforms generally to the formula:

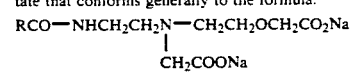

[c]Commercially available from Dr. Madis Laboratories, Inc., South Hackensack, New Jersey as Veragel ® Liquid 1:10
[d]Polyhexamethylene biguanide hydrochloride; commercially available from ICI Americas Inc. (See general formula of active disclosed hereinbefore)

The aqueous composition of Example 1 exhibited excellent preservative activity in a 4 week challenge test against *Staphylococcus aureus,* Pseudomonas product isolate, yeast product isolate and *Aspergillus niger.*

Moistened wipes in accordance with the invention were prepared by impregnating a flexible absorbent nonwoven substrate with 350% of its weight of the aqueous composition of Example 1. A gravity application procedure was employed as follows:

The aqueous composition of Example 1 (196 g) was placed in a cylindrical canister and a coreless roll of flexible absorbent nonwoven fabric (56 g) comprised of 40 dry wipes (5.75"×8.0") was placed in the canister with one end immersed in the liquid. The canister was capped with a plastic cap and was then inverted and maintained in the inverted position for a minimum of three days to ensure complete absorbtion and uniform distribution of the aqueous composition into the coreless roll of fabric. The canister then was inverted to the upright position.

The flexible absorbent nonwoven fabric employed in the foregoing procedure for making the moist wipes was a 70/30 blend of rayon and polyester fibers which was processed into uniform web form by a carding machine. The web then was saturated with an aqueous dilution of an acrylic binder (available commercially from Rohm and Haas Company, Inc., Philadelphia, Pa. under the tradename Rhoplex NW-1402), the amount of binder being such as to provide 20% w/w of the finished nonwoven fabric. The treated web was then dried and heated to 300° F. to cure the binder. The finished nonwoven fabric, having a basis weight of 40 g/sq. yd., was then slit and cut into the desired dimension.

The moistened wipes so obtained were quite acceptable with respect to slippery feel and were completely protected against contamination by the molds *Aspergillus niger* and *Eupenicillium levitum* in a 6 months challenge test.

EXAMPLE 2

An aqueous composition according to the invention was prepared identical to the composition of Example 1 except that poly[oxyethylene(dimethyliminio)ethylene(dimethyliminio)ethylene dichloride] (commercially available under the tradename WSCP from Buckman Laboratories Inc. - see description hereinbefore) was employed on a weight for weight active basis instead of Cosmocil CQ.

Moistened wipes were prepared employing the aqueous composition of Example 2 as impregnant using the identical substrate and gravity application procedure described hereinbefore for the preparation of the moistened wipes impregnated with the composition of Example 1. These wipes also were quite acceptable with respect to slippery feel.

Seven aqueous compositions were prepared which were identical to the aqueous composition of Example 1 with the exception that on a weight for weight active basis one of the following seven commercially available biocides was employed instead of Cosmocil CQ:

Composition A: N-alkyl(50% $C_{14}$, 40% $C_{12}$, 10% $C_{16}$,) dimethyl benzyl ammonium chloride Composition B: Cetyl pyridinium chloride Composition C: Didecyl dimethyl ammonium chloride Composition D: 1-Hydroxyethyl-1-benzyl-2-alkyl(-coco)imidazolinium chloride Composition E: Diisobutylphenoxyethoxyethyl dimethyl benzyl ammonium chloride Composition F: Poly(dimethyl butenyl ammonium chloride)-α, ω-bis-triethanolammonium chloride Composition G: Quaternium-33 which conforms to the formula:

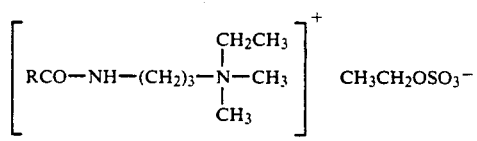

where RCO— represents the lanolin acid radical.

Moistened wipes were prepared employing Composition A to G above as impregnant using the identical substrate and gravity procedure described hereinbefore for the preparation of the moistened wipes impregnated with the composition of Example 1. In each case the moistened wipes obtained had an unacceptable slippery feel which rendered them unsuitable for marketing.

What is claimed is:

1. A moistened wipe for cleaning and delivering a cationic biocide to animate or inonius surfaces comprising a flexible absorbent nonwoven substrate impregnated with an aqueous composition comprising from about 0.02 to about 0.25 weight-percent of potassium sorbate, from about 0.05 to about 0.20 weight-percent of citric acid, from about 0.02 to about 0.20 weight-percent of disodium ethylenediaminetetraacetate, from about 0.03 to about 0.24 weight-percent of a cationic biocide selected from the group consisting of (a) polyhexamethylene biguanide hydrochloride and (b) poly[oxyethylene(dimethylimino)ethylene(dimethylimino)ethylene dichloride]; and the remainder to 100 weight-percent water, wherein the pH of the composition is from about 3.5 to about 4.5.

2. The moistened wipe of claim 1, wherein the loading of the aqueous composition on the substrate is from about 200 to about 500 percent by weight of the substrate.

3. The moistened wipe of claim 1 wherein the cationic biocide is polyhexamethylene biguanide hydrochloride.

4. The moistened wipe of claim 3 wherein the weight-percent of potassium sorbate is about 0.140, the weight-percent of citric acid is about 0.100, the weight-percent of disodium EDTA is about 0.090 and the weight-percent of the cationic biocide is about 0.140.

5. The moistened wipe of claim 1 wherein the cationic biocide is poly[oxyethylene(dimethyliminio)ethylene(dimethyliminio)ethylene dichloride].

6. The moistened wipe of claim 5 wherein the weight-percent of potassium sorbate is about 0.140, the weight-percent of citric acid is about 0.100, the weight-percent of disodium EDTA is about 0.090 and the weight-percent of the cationic biocide is about 0.140.

7. The moistened wipe of claim 1 wherein the pH is from about 4.0 to about 4.3.

8. The moistened wipe of claim 1 which additionally contains an ingredient selected from the group consisting of a skin moisturizer, a skin softener and a surfactant and mixtures of such ingredients.

9. The moistened wipe of claim 8 wherein the cationic biocide is polyhexamethylene biguanide hydrochloride.

10. The moistened wipe of claim 9 wherein the weight-percent of potassium sorbate is about 0.140, the weight-percent of citric acid is about 0.100, the weight-percent of disodium EDTA is about 0.090 and the weight-percent of the cationic biocide is about 0.140, and which additionally contains about 0.500 weight-percent of propylene glycol, about 0.050 weight-percent of PEG-60 lanolin and about 0.038 weight-percent of cocoamphodiacetate.

11. The moistened wipe of claim 10 wherein the loading of the aqueous composition on the substrate is about 350% of the weight of the substrate.

12. The moistened wipe of claim 8 wherein the cationic biocide is poly[oxyethylene(dimethyliminio)ethylene(dimethyliminio)ethylene dichloride].

13. The moistened wipe of claim 12 wherein the weight-percent of potassium sorbate is about 0.140, the weight-percent of citric acid is about 0.100, the weight percent of disodium EDTA is about 0.090 and the weight-percent of the cationic biocide is about 0.140, and which additionally contains about 0.500 weight-percent of propylene glycol, about 0.050 weight-percent of PEG-60 lanolin and about 0.038 weight-percent of cocoamphodiacetate.

14. The moistened wipe of claim 13 wherein the loading of the aqueous composition on the substrate is about 350% of the weight of the substrate.

* * * * *

UNITED STATES PATENT AND TRADEMARK OFFICE
CERTIFICATE OF CORRECTION

PATENT NO. : 5,141,803

DATED : August 25, 1992

INVENTOR(S) : David Pregozen

It is certified that error appears in the above-identified patent and that said Letters Patent is hereby corrected as shown below:

On the title page, under references cited, Class/Subclass
U.S. Patent Documents Reference 4,017,002 4/1977
Doyle et al. 221/63 should be added.

Column 7, line 47 "inonius" should read inanimate

Signed and Sealed this

Twenty-third Day of November, 1993

*Attest:*

BRUCE LEHMAN

*Attesting Officer*     *Commissioner of Patents and Trademarks*